United States Patent
Okamoto et al.

(10) Patent No.: US 7,199,253 B2
(45) Date of Patent: Apr. 3, 2007

(54) METHOD OF MANUFACTURING ALKYLENE CARBONATE

(75) Inventors: Hiroshige Okamoto, Okayama (JP); Ken Someya, Kurashiki (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 10/558,742

(22) PCT Filed: May 28, 2004

(86) PCT No.: PCT/JP2004/007744

§ 371 (c)(1),
(2), (4) Date: Dec. 1, 2005

(87) PCT Pub. No.: WO2004/108696

PCT Pub. Date: Dec. 16, 2004

(65) Prior Publication Data

US 2006/0281929 A1   Dec. 14, 2006

(30) Foreign Application Priority Data

Jun. 4, 2003   (JP) .............................. 2003-159326

(51) Int. Cl.
*C07D 317/38* (2006.01)
(52) U.S. Cl. .................................................... 549/230
(58) Field of Classification Search ................. 549/230
See application file for complete search history.

(56) References Cited

FOREIGN PATENT DOCUMENTS

| EP | 0 628 554 | 5/1994 |
|---|---|---|
| EP | 1 034 824 | 9/2000 |
| GB | 2 011 402 | 7/1979 |
| JP | 50-14632 | 2/1975 |
| JP | 54-97865 | 8/1979 |
| JP | 6-345698 | 12/1994 |
| JP | 2000-266477 | 9/2000 |

OTHER PUBLICATIONS

Akiyoshi Tamaoki et al., "Kagaku Puranto Kensetsu Binran (Handbook for Building Chemical Plants)" published by Maruzen co., Ltd., Japan on Nov. 30, 1980, pp. 1305-1306.
International Search Report mailed Sep. 21, 2004.

*Primary Examiner*—Bernard Dentz
(74) *Attorney, Agent, or Firm*—Staas & Halsey LLP (57) ABSTRACT

A process for producing an alkylene carbonate, which comprises reacting an alkylene oxide with carbon dioxide in the presence of a catalyst in a reactor to obtain a reaction mixture containing an alkylene carbonate, the reactor communicating with a process-side channel of a heat exchanger through a piping to form a circulation circuit, wherein the process is characterized in that it further comprises, during or after the reaction, flowing a process liquid through the circulation circuit including the reactor and the process-side channel of the heat exchanger while flowing a heat exchange medium having a temperature of from 140° C. to 200° C. through the heat exchange-side channel of the heat exchanger, thereby maintaining the inner temperature of the process-side channel at 135° C. to 200° C.

6 Claims, 1 Drawing Sheet

Figure

METHOD OF MANUFACTURING ALKYLENE CARBONATE

This application is national stage entry of PCT/JP04/07744 filed May 28, 2004.

BACKGROUND OF THE INVENTION

1. Field of the Invention

The present invention relates to a process for producing an alkylene carbonate. More particularly, the present invention is concerned with a process for producing an alkylene carbonate, which comprises reacting an alkylene oxide with carbon dioxide in the presence of a catalyst in a reactor to obtain a reaction mixture containing an alkylene carbonate, the reactor communicating with a process-side channel of a heat exchanger through a piping to form a circulation circuit, wherein the process is characterized in that it further comprises, during or after the reaction, flowing a process liquid through the circulation circuit including the reactor and the process-side channel of the heat exchanger while flowing a heat exchange medium having a temperature of from 140° C. to 200° C. through the heat exchange-side channel of the heat exchanger, thereby maintaining the inner temperature of the process-side channel at a level within the range of from 135° C. to 200° C. By the use of the process of the present invention, it becomes possible to prevent foulings from occurring on the inner wall of the process-side channel of the heat exchanger or wash-away fouls having occurred and adhered to the inner wall of the process-side channel of the heat exchanger. Therefore, the heat removing ability of the heat exchanger is not lowered, thereby enabling the stable, continuous production of an alkylene carbonate for a long period of time.

2. Prior Art

The reaction for producing an alkylene carbonate by reacting an alkylene oxide with carbon dioxide in the presence of a catalyst is a liquid phase reaction, and it generates a heat of reaction in a quantity as large as 96.23 kJ/mol. Therefore, in the commercial scale production of an alkylene carbonate, stable removal of the heat of reaction is especially important for the stable operation and safety of the production process. Generally, in the production of an alkylene carbonate, a heat exchanger is used for removing the heat of reaction. However, when the operation of the production system for producing an alkylene carbonate by reacting an alkylene oxide with carbon dioxide in the presence of a catalyst is continued for a certain period of time, foulings occur on the inner wall of the process-side channel of the heat exchanger, thereby lowering the heat removing ability of the heat exchanger. Due to such lowering of the heat removing ability of the heat exchanger, the conventional process has a problem in that it is difficult to produce an alkylene carbonate stably in a continuous manner.

For example, in the working examples of Unexamined Japanese Patent Application Laid-Open Specification No. Sho 50-14632, a double-wall heat exchanger or a multi-tube heat exchanger is used to remove the heat of reaction generated during the production of an alkylene carbonate. The production system used in this patent document comprises first to third reactors, and the production system is operated under conditions such that the reaction temperature of the first reactor is 175° C. and the reaction temperature of each of the second and third reactors is 180° C. However, this patent document has no description about a cooling medium fed to the heat exchanger and the temperature thereof. Further, a method for preventing foulings from occurring in the heat exchanger is not described in this patent document.

In the working examples of Unexamined Japanese Patent Application Laid-Open Specification No. Sho 54-98765, an alkylene carbonate was produced using a circulation circuit comprising a reactor and a heat exchanger. Specifically, for controlling the reaction temperature so that the temperature measured at the outlet of the reactor becomes 190° C., this patent document describes that water having a temperature of 110° C. was fed as a cooling medium to the cooling-side channel of the heat exchanger and that, as a result, steam (heat-exchanged cooling medium) discharged from the heat exchanger had a temperature of 160° C. or 170° C. However, this patent document also has no description about a method to prevent foulings from occurring in the heat exchanger.

In addition, although each of the above-mentioned patent documents describes a method for removing the heat of reaction generated during the production of an alkylene carbonate by means of a heat exchanger, the documents have no description about a chemical washing method for easily washing-away fouls having adhered to the inner wall of the process-side channel of the heat exchanger.

As conventional methods for cleaning and washing a heat exchanger, there can be mentioned mechanical washing methods in which fouls having adhered to the inner wall of the process-side channel of the heat exchanger are removed therefrom after disassembling the heat exchanger into parts thereof; and chemical washing methods in which fouls having adhered to the inner wall of the process-side channel of the heat exchanger are dissolved or stripped off with a chemical reagent without disassembling the heat exchanger. Specific examples of mechanical washing methods include a method in which the inner wall of a tube of the heat exchanger is washed using a brush, drill or the like which is driven by an electric power or an air motor; a method in which water is pressurized to 20 to 30 MPa using a high pressure pump and sprayed therethrough a small nozzle to thereby forcibly strip-off and wash-away the fouls from the heat exchanger; and a sand blast method in which sand (or iron particles) is sprayed onto the fouls by using highly pressurized air to thereby blow-off the fouls from the heat exchanger. For performing the chemical washing method, it is necessary to choose an appropriate material and conditions, e.g., the type and amount of a chemical reagent used as a washing liquid, a washing temperature and a washing method, depending on the type of fouls adhering to a heat exchanger (see, for example, pp. 1305–1306 of Akiyoshi Tamaoki ed., "Kagaku Puranto Kensetsu Binran (Handbook for Building Chemical Plants)" published by Maruzen Co., Ltd., Japan on Nov. 30, 1980, 7th printing). With respect to the washing of a heat exchanger which has been used for producing an alkylene carbonate, only mechanical washing methods have been practically used and, heretofore, neither an effective chemical reagent nor an effective chemical washing method is known in the art.

SUMMARY OF THE INVENTION

In this situation, the present inventors have made extensive and intensive studies for developing a process for continuously and stably producing an alkylene carbonate by either preventing foulings from occurring on the inner wall of the process-side channel of a heat exchanger or easily washing-away fouls having occurred and adhered to the inner wall of the process-side channel of the heat exchanger, wherein the fouls cause the lowering of the heat removing ability of the heat exchanger. As a result, it has unexpectedly been found that a considerable amount as large as a little more than 40% by weight of the fouls which adhere to the inner wall of the process-side channel of the heat exchanger during the production of an alkylene carbonate are decomposed and volatilized at 116° C. to 165° C. Based on this finding, with respect to a process for producing an alkylene carbonate, which comprises reacting an alkylene oxide with carbon dioxide in a reactor communicating with a process-side channel of a heat exchanger through a piping to form a circulation circuit, the present inventors have successfully developed a new technique which can be used to prevent foulings from occurring on the inner wall of the process-side channel of a heat exchanger or easily wash-away fouls having occurred and adhered to the inner wall of the process-side channel of the heat exchanger. The abovementioned new technique is to flow a process liquid through the circulation circuit including the reactor and the process-side channel of the heat exchanger during or after the reaction, while flowing a heat exchange medium having a temperature of from 140° C. to 200° C. through the heat exchange-side channel of the heat exchanger, to thereby maintain the inner temperature of the process-side channel at a level within the range of from 135° C. to 200° C. The present invention has been completed, based on these novel findings.

Accordingly, it is a primary object of the present invention to provide a process for producing an alkylene carbonate, which is advantageous in that a lowering of the heat removing ability of the heat exchanger is prevented by either preventing foulings from occurring on the inner wall of the process-side channel of the heat exchanger or easily washing-away fouls having occurred and adhered to the inner wall of the process-side channel of the heat exchanger, so that the continuous production of an alkylene carbonate can be performed stably for a long period of time.

The forgoing and other objects, features and advantages of the present invention will be apparent to those skilled in the art from the following detailed description and appended claims taken in connection with the accompanying drawing.

DESCRIPTION OF REFERENCE NUMERALS

1: carbon dioxide feeding pump
2: ethylene oxide feeding pump
3: catalyst feeding pump
4: carbon dioxide evaporator
5 to 8, 11, 12, 15, 18, 19, 21, 22, 24 to 26: pipe
9: circulation pump of reactor
10: reactor
13: circulation flow meter of reactor
14: heat exchanger
16: temperature control valve of reactor
17: flow meter for heat exchange medium
20: control valve for withdrawing a reaction mixture
23: gas control valve at a vent of reactor
T1, T2, t1 and t2: thermometer

DETAILED DESCRIPTION OF THE INVENTION

In one aspect of the present invention, there is provided a process for producing an alkylene carbonate, which comprises reacting an alkylene oxide represented by the following formula (1):

wherein each of $R^1$, $R^2$, $R^3$ and $R^4$ independently represents a hydrogen atom, a $C_1$–$C_8$ straight chain hydrocarbon group, a $C_3$–$C_8$ alicyclic hydrocarbon group or a $C_6$–$C_8$ aromatic hydrocarbon group, with carbon dioxide in the presence of a catalyst in a reactor to obtain a reaction mixture in the reactor, wherein the reaction mixture contains an alkylene carbonate represented by the following formula (2):

wherein $R^1$, $R^2$, $R^3$ and $R^4$ are as defined for formula (1), the reactor communicating with a process-side channel of a heat exchanger through a piping to form a circulation circuit, wherein the heat exchanger has a heat exchange-side channel for flowing therethrough a heat exchange medium having a temperature controlled in a predetermined range and has the process-side channel for flowing therethrough a process liquid which is heat exchanged with the heat exchange medium in association with the process for producing an alkylene carbonate, characterized in that the process further comprises, during or after the reaction, flowing the process liquid through the circulation circuit including the reactor and the process-side channel of the heat exchanger while flowing the heat exchange medium having a temperature of from 140° C. to 200° C. through the heat exchange-side channel of the heat exchanger, thereby maintaining the inner temperature of the process-side channel at a level within the range of from 135° C. to 200° C.

For the easy understanding of the present invention, essential features and various preferred embodiments of the present invention are enumerated below.
1. A process for producing an alkylene carbonate, which comprises reacting an alkylene oxide represented by the following formula (1):

wherein each of $R^1$, $R^2$, $R^3$ and $R^4$ independently represents a hydrogen atom, a $C_1$–$C_8$ straight chain hydrocarbon group, a $C_3$–$C_8$ alicyclic hydrocarbon group or a $C_6$–$C_8$ aromatic hydrocarbon group, with carbon dioxide in the presence of a catalyst in a reactor to obtain a reaction mixture in the reactor, wherein the reaction mixture contains an alkylene carbonate represented by the following formula (2):

(2)

wherein $R^1$, $R^2$, $R^3$ and $R^4$ are as defined for formula (1), the reactor communicating with a process-side channel of a heat exchanger through a piping to form a circulation circuit, wherein the heat exchanger has a heat exchange-side channel for flowing therethrough a heat exchange medium having a temperature controlled in a predetermined range and has the process-side channel for flowing therethrough a process liquid which is heat exchanged with the heat exchange medium in association with the process for producing an alkylene carbonate, characterized in that the process further comprises, during or after the reaction, flowing the process liquid through the circulation circuit including the reactor and the process-side channel of the heat exchanger while flowing the heat exchange medium having a temperature of from 140° C. to 200° C. through the heat exchange-side channel of the heat exchanger, thereby maintaining the inner temperature of the process-side channel at a level within the range of from 135° C. to 200° C.

2. The process according to item 1 above, wherein, during the reaction, the reaction mixture obtained by the reaction of an alkylene oxide with carbon dioxide is flowed as the process liquid.
3. The process according to item 1 above, wherein, after the reaction, a washing liquid is flowed as the process liquid.
4. The process according to any one of items 1 to 3 above, wherein the alkylene oxide is ethylene oxide and the alkylene carbonate is ethylene carbonate.

Hereinbelow, the present invention will be described in more detail.

The reaction of an alkylene oxide with carbon dioxide which is performed in the presence of a catalyst to produce an alkylene carbonate is an exothermic reaction. Therefore, in the commercial scale production of an alkylene carbonate, the heat of reaction is generally removed by means of a heat exchanger. However, when the production of an alkylene carbonate is continued for a certain period of time, foulings are likely to occur on the inner wall of the process-side channel of the heat exchanger. As a result, the heat removing ability of the heat exchanger becomes lowered and it becomes difficult to produce the alkylene carbonate stably in a continuous manner. Further, the occurrence of the foulings poses another problem in that the washing of a heat exchanger having fouls adhered thereto is not only time consuming, but also laborious. The present inventors have made extensive and intensive studies for solving these problems.

Firstly, the present inventors analyzed the properties of the fouls which have adhered to a process-side channel of a heat exchanger and caused the heat removing ability of the heat exchanger to lower. Specifically, the present inventors performed a continuous production of ethylene carbonate for 30 days using a conventional production system and, then, dismounted a strainer from the circulation pump of the reactor (which strainer can be easily overhauled) to examine the interior of the strainer. As a result, it has been found that a very small amount of membranous elastic fouls comprising viscous polymeric substances and the like (hereinafter, frequently referred to simply as "fouls") occurred and adhered to the inner wall of the strainer at the bottom portion thereof, where the temperature during the operation of the production system is relatively low due to heat dissipation. The very small amount of the fouls found in the strainer was taken as a sample to be subjected to various tests and analyses.

FT-IR microscopic examination of the fouls comprising viscous polymeric substances was performed by means of an infrared spectrometer (FTS-575C/UMA-500, manufactured and sold by Bio-Rad Laboratories, U.S.A.). From the results of the FT-IR microscopic examination, the fouls were presumed to be a mixture of compounds having a carbonyl linkage, an ester linkage, an ether linkage and the like. Further analysis of the fouls revealed that the fouls were composed of a polymer mixture mainly containing ethylene glycol units and ethylene carbonate units and an esterified product thereof.

In order to find a substance which is capable of easily dissolving the viscous polymeric substances, thereby enabling an easy chemical washing of the heat exchanger, the present inventors tried dissolution tests with respect to the fouls using various chemical reagents, such as acetone, methanol, toluene, benzyl alcohol, ethyl acetate, hot water having a temperature of 100° C., 1N NaOH, 1N HCl, dimethyl formamide (DMF), tetrahydrofuran (THF), o-dichlorobenzene and ethylene carbonate. However, none of the chemical reagents were able to dissolve the fouls.

Next, analysis by differential scanning calorimetry (DSC) of the fouls was performed by means of a low temperature differential scanning calorimeter (DSC-220C, manufactured and sold by Seiko Instruments Inc., Japan) under cycle testing conditions wherein the rate of temperature elevation was 10° C./minute and the scanning temperature ranged from room temperature to 360° C. As a result, it has surprisingly been found that, when the scanning temperature was elevated from room temperature to 360° C., clear endothermic peaks were observed around 135° C. and around 223° C., but when the scanning temperature was lowered from 360° C. to room temperature and, then, elevated to 360° C. again, the above-mentioned two endothermic peaks disappeared completely.

Further, the change in weight of the fouls was determined by means of a thermogravimetric/differential thermal analyzer (TG/DTA-220, manufactured and sold by Seiko Instruments Inc., Japan) under cycle testing conditions wherein the rate of temperature elevation was 10° C./minute and the measuring temperature ranged from room temperature to 600° C. As a result, it was found that the decrease in weight of the fouls at 116° C. or lower, which change is considered to be caused by the evaporation of moisture from the fouls, was 20%. Further elevation of the temperature caused the decomposition of the fouls, and the weight loss of 43% was observed over the temperature range of from 116° C. to 165° C., the weight loss of 25% was observed over the temperature range of from 165° C. to 411° C.; however, no further weight loss was observed over the temperature range of from 441° C. to 600° C. These results show that a little more than 40% of the fouls having adhered to the heat exchanger can be decomposed and volatilized over the relatively low temperature range of from 116° C. to 165° C.

Based on the observations on the occurrence of foulings in the heat exchanger and the results of the above-mentioned analyses, the present inventors presumed that, when the temperature of a heat exchange medium supplied to and flowing through the heat exchange-side channel of the heat exchanger is low (lower than 140° C.), the surface temperature of the heat transfer tube as the process side-channel of the heat exchanger becomes lowered and foulings of the polymeric substances and the like on the inner wall of the heat exchange tube are likely to occur, wherein the foulings cause a lowering of the heat removing ability of the heat exchanger. Further, based on this presumption, the present inventors made the following hypothesis. The fouls which have adhered to the inner wall of the process-side channel of the heat exchanger would be effectively removed by a chemical washing method in which a washing liquid is charged into a reactor and flowed through the circulation circuit while maintaining the inner temperature of the process-side channel of the heat exchanger at a level within the range of from 116 to 165° C. Specifically, by this chemical washing method, the fouls would be easily decomposed, and even fouls which have not been decomposed at the above-mentioned temperature would lose their viscosity, so that the fouls come off the heat exchanger and diffuse into the washing liquid. To prove this hypothesis, the present inventors made an attempt to wash-away fouls having adhered to the inner wall of the process-side channel of the heat exchanger by the above-mentioned method using water and ethylene carbonate as washing liquids. As a result, it was confirmed that both water and ethylene carbonate were able to wash-away fouls having adhered to the inner wall of the process-side channel of the heat exchanger, so that the heat exchanger completely regained its heat removing ability.

Then, the present inventors made studies on a method for preventing foulings from occurring in the heat exchanger during the production of an alkylene carbonate so that an alkylene carbonate can be stably produced for a long period of time. Firstly, to specify the conditions under which foulings would not occur and even fouls which are formed and adhered to the inner wall of the process-side channel of the heat exchanger would be decomposed and easily come off the inner wall, so that a lowering of the heat removing ability of a heat exchanger can be prevented, the present inventors performed tests in which an alkylene carbonate was produced while stepwise elevating the temperature of the heat exchange medium fed. As a result, it has surprisingly been found that, when the temperature of the heat exchange medium flowing through the heat exchange-side channel of the heat exchanger is elevated to 140° C., no further decrease in heat removing ability of the heat exchanger was observed, and that, when the temperature of the heat exchange medium was further elevated to 145° C., the overall heat transfer coefficient (U) of the heat exchanger increased gradually and the heat removing ability recovered to the initial level.

The reason why the heat removing ability does not become lowered when the temperature of the heat exchange medium flowing through the heat exchange-side channel of the heat exchanger is elevated to 140° C. is considered as follows. When the heat exchange medium having a temperature of 140° C. or more is flowed through the heat exchange-side channel of the heat exchanger, the surface temperature of the process-side channel of the heat exchanger reaches 135° C. or higher, thereby preventing foulings of the polymeric substances and the like from occurring on the inner wall of the process-side channel of the heat exchanger. Further, when the temperature of the heat exchange medium fed to the heat exchanger is elevated to 145° C., the heat removing ability recovers because the small amount of fouls having adhered to the inner wall of the process-side channel of the heat exchanger is heat-decomposed into low molecular weight substances and the residual fouls (such as polymeric substances) are converted into substances which easily come off the inner wall. The resultant very small particles are diffused into the reaction mixture, so that the heat exchanger regains its heat removing ability. The present invention has been completed, based on these novel findings.

As mentioned above, according to the present invention, there is provided a process for producing an alkylene carbonate, which comprises reacting an alkylene oxide represented by the following formula (1):

(1)

wherein each of $R^1$, $R^2$, $R^3$ and $R^4$ independently represents a hydrogen atom, a $C_1$–$C_8$ straight chain hydrocarbon group, a $C_3$–$C_8$ alicyclic hydrocarbon group or a $C_6$–$C_8$ aromatic hydrocarbon group, with carbon dioxide in the presence of a catalyst in a reactor to obtain a reaction mixture in the reactor, wherein the reaction mixture contains an alkylene carbonate represented by the following formula (2):

(2)

wherein $R^1$, $R^2$, $R^3$ and $R^4$ are as defined for formula (1), the reactor communicating with a process-side channel of a heat exchanger through a piping to form a circulation circuit, wherein the heat exchanger has a heat exchange-side channel for flowing therethrough a heat exchange medium having a temperature controlled in a predetermined range and has the process-side channel for flowing therethrough a process liquid which is heat exchanged with the heat exchange medium in association with the process for producing an alkylene carbonate, characterized in that the process further comprises, during or after the reaction, flowing the process liquid through the circulation circuit including the reactor and the process-side channel of the heat exchanger while flowing the heat exchange medium having a temperature of from 140° C. to 200° C. through the heat exchange-side channel of the heat exchanger, thereby maintaining the inner temperature of the process-side channel at a level within the range of from 135° C. to 200° C.

An alkylene oxide which is a raw material for producing an alkylene carbonate in the process of the present invention is a compound represented by the following formula (1):

(1)

wherein each of $R^1$, $R^2$, $R^3$ and $R^4$ independently represents a hydrogen atom, a $C_1$–$C_8$ straight chain hydrocarbon group, a $C_3$–$C_8$ alicyclic hydrocarbon group or a $C_6$–$C_8$ aromatic hydrocarbon group.

Specific examples of such alkylene oxides include ethylene oxide, propylene oxide, butylene oxide, vinylethylene oxide, cyclohexene oxide and styrene oxide. From the viewpoint of availability and the like, ethylene oxide and propylene oxide are especially preferred.

In the process of the present invention, the above-mentioned alkylene oxide is reacted with carbon dioxide in the presence of a catalyst in a reactor to obtain a reaction mixture in the reactor. The obtained reaction mixture contains an alkylene carbonate represented by the following formula (2):

(2)

wherein $R^1$, $R^2$, $R^3$ and $R^4$ are as defined for formula (1).

Specific examples of alkylene carbonates include ethylene carbonate, propylene carbonate, butylene carbonate, vinylethylene carbonate, cyclohexene carbonate and styrene carbonate. The process of the present invention can be preferably used for producing ethylene carbonate and propylene carbonate.

The reaction of an alkylene oxide with carbon dioxide, which is involved in the process of the present invention for producing an alkylene carbonate, can be represented by the following formula (3):

wherein $R^1$, $R^2$, $R^3$ and $R^4$ are as defined for formula (1).

In the process of the present invention, an alkylene oxide is reacted with carbon dioxide in the presence of a catalyst. There is no particular limitation with respect to the catalyst used in the present invention so long as the catalyst is one which is generally used to catalyze the reaction represented by formula (3) above. Specific examples of such catalysts include organic compound catalysts, such as tetraethylammonium bromide, halides of 5- or 6-membered ring hydrocarbons, ammonium rhodanide and heat decomposition products thereof; and inorganic compound catalysts, such as metals, bromides or iodides of alkali metals, and mixtures thereof with a small amount of an alcohol or water. From the viewpoint of the ease in the recovery of the catalyst, the inorganic catalyst is preferred. There is no particular limitation with respect to the amount of the catalyst used, but it is preferred that the catalyst concentration of the reaction system is 0.1 to 3% by weight, more preferably 0.1 to 2% by weight.

The reaction temperature for producing an alkylene carbonate is generally in the range of from 100° C. to 200° C., preferably from 150° C. to 190° C. The reaction pressure is generally in the range of from 2 MPa to 15 MPa, preferably from 4 MPa to 12 MPa. The reaction time may vary depending on the proportions of the raw materials (i.e., ratio of the carbon dioxide to the alkylene oxide), the type of the alkylene oxide used, the type and concentration of the catalyst used, the reaction temperature and the like. For example, when the reaction time is defined as the average retention time calculated from the retention volume and the total feed volume of a continuously stirring tank reactor, the reaction time is generally 0.5 hours to 10 hours, preferably 1 hour to 5 hours.

When the process of the present invention is put into practice, the alkylene oxide and carbon dioxide as raw materials are used in amounts such that the molar ratio of the carbon dioxide to the alkylene oxide is generally in the range of from 1 to 5, preferably 1 to 2. In general, when excess carbon dioxide gas is discharged from the reactor, the unreacted alkylene oxide is also discharged from the reactor in such a form as entrained by the carbon dioxide gas, thereby increasing the amount of the alkylene oxide discharged from the reactor. Therefore, as a method for controlling the molar ratio of carbon dioxide to the alkylene oxide in the reactor, it is not preferred to discharge excess carbon dioxide gas from the reactor, and it is preferred to control the amount of carbon dioxide fed to the reactor so as to maintain the pressure of the reactor at a constant value.

The reactor used in the process of the present invention for performing the above-mentioned reaction communicates with a process-side channel of a heat exchanger through a piping to form a circulation circuit. In the present invention, any of conventional reactors can be used. Examples of conventional reactors include a continuously stirring type tank reactor, a multi-stage reactor formed by connecting a plurality of continuously stirring type tank reactors in series, a plug flow reactor, a combination of a continuously stirring type tank reactor and a plug flow reactor.

When an alkylene carbonate is produced using a continuously stirring type tank reactor, it is preferred that a large amount of the reaction mixture is circulated in the circulation circuit by using a pump so as to enable the carbon dioxide gas to be dissolved into the reaction mixture. In general, the number of circulation performed per unit time is 10 to 50 times/hour, preferably 20 to 40 times/hour. When the heat of reaction is removed by means of a heat exchanger which is provided in the middle of a piping through which the reaction mixture is flowed using a pump, circulation of a large amount of the reaction mixture is preferred from the viewpoint of the improvement in the cooling ability of the heat exchanger.

The heat exchanger used in the present invention has a heat exchange-side channel for flowing therethrough a heat exchange medium having a temperature controlled in a predetermined range and has a process-side channel for flowing therethrough a process liquid which is heat exchanged with the heat exchange medium in association with the process for producing an alkylene carbonate. In the present invention, the "process liquid" is defined as a liquid which is processed (i.e., subjected to temperature control) in the heat exchanger, and the "heat exchange medium" is a medium used to control the temperature of the process liquid. Further, the "heat exchange-side channel" of the heat exchanger is a channel for flowing therethrough the heat exchange medium, and the "process-side channel" of the heat exchanger is a channel for flowing therethrough a process liquid. There is no particular limitation with respect to the heat exchanger used in the process of the present invention so long as the heat exchanger is capable of flowing a heat exchange medium having a temperature of from 140° C. to 200° C. through the heat exchange-side channel of the heat exchanger, to thereby maintain the inner temperature of the process-side channel at a level within the range of from 135° C. to 200° C. For example, a coil-type heat exchanger provided inside a reactor, a double-wall heat exchanger and a conventional multi-tube heat exchanger can be used either individually or in combination. A multi-tube heat exchanger which is capable of increasing the heat transfer area and may be small in size is preferred in the present invention.

When a multi-tube heat exchanger (which comprises a shell having accommodated therein a plurality of tubes) is used in the present invention, the process liquid and the heat exchange medium may be flowed through the tubes and the shell space (i.e., space between the tubes and the inner wall of the shell), respectively, or, alternatively, through the shell space and the tubes, respectively. With respect to the determination as to which of the fluids (the process liquid and the heat exchange medium) should be flowed through the tubes or the shell space, such determination can be made appropriately, taking into consideration various factors. For example, when a small heat exchanger is used, the fluid which is flowed through the tubes of the heat exchanger can be selected so as to increase the overall heat transfer coefficient (U), and when there is a need to facilitate the washing of the heat exchanger, a fluid which is more likely to cause foulings can be flowed through the tubes of the heat exchanger.

It is preferred that the heat exchanger used in the present invention is an apparatus which can be used as both a preheating device and a cooling device. Such a heat exchanger can be used as a preheating device at the start of the reaction for heating the reaction mixture to a predetermined reaction temperature and as a cooling device for removing the heat of reaction during the stationary operation of the production system.

There is no particular limitation with respect to the material used to produce the process-side channel of the heat exchanger so long as the material is resistant to corrosion by the process liquid. Iron rusts may cause the formation of alkylene oxide polymers by its catalytic activity and, therefore, it is preferred that the process-side channel of the heat exchanger is made of a material, such as stainless steel, which is free from the danger of formation of the iron rusts.

There is no particular limitation with respect to the heat exchange medium so long as the heat exchange medium is capable of maintaining its temperature at a level within the range of from 140° C. to 200° C., preferably from 140° C. to 180° C. Any of the substances which are conventionally used as a heat exchange medium, such as water, steam and heat transfer oil, can be used. A heat transfer oil which is thermally stable and has a low vapor pressure is preferred since the pressure of the heat exchanger can be designed at a low level. Further, the temperature of the heat transfer oil can be controlled easily, so that when the heat transfer oil is used as the heat exchange medium, the reaction temperature can be controlled simply by changing the amount of the heat exchange medium fed to the heat exchanger. As a result, the use of the heat exchange oil facilitates the operation of the alkylene carbonate production system.

A fundamental difference between the process of the present invention and the prior art resides in that the temperature of the heat exchange medium fed to the heat exchanger is maintained at a level within a specific range. In the process of the present invention, during or after the reaction of an alkylene oxide with carbon dioxide for producing an alkylene carbonate, the process liquid is flowed through the circulation circuit including the reactor and the process-side channel of the heat exchanger while flowing the heat exchange medium having a temperature of from 140° C. to 200° C., preferably from 140° C. to 180° C., through the heat exchange-side channel of the heat exchanger, thereby maintaining the inner temperature of the process-side channel at a level within the range of from 135° C. to 200° C., preferably from 140° C. to 180° C. In a preferred embodiment of the present invention, during the above-mentioned reaction, the reaction mixture obtained by the reaction of an alkylene oxide with carbon dioxide is flowed as the process liquid to thereby prevent foulings from occurring on the inner wall of the process-side channel of the heat exchanger. Alternatively, after the reaction, a washing liquid is flowed as the process liquid to thereby wash-away fouls having adhered to the inner wall of the process-side channel of the heat exchanger. When an alkylene carbonate is produced by such a process of the present invention, it becomes possible to produce an alkylene carbonate stably for a long period of time, irrespective of the structure of the heat exchanger or the type of the heat exchange medium.

There is no particular limitation with respect to the temperature of the heat exchange medium which is flowed through the heat exchange-side channel of the heat exchanger during the reaction of an alkylene oxide with carbon dioxide for producing an alkylene carbonate. From the viewpoint of preventing foulings from occurring on the inner wall of the process-side channel of the heat exchanger, it is preferred that the temperature of the heat exchange medium is high, because the higher the temperature of the heat transfer medium, the higher the inner temperature of the process-side channel of the heat exchanger. An appropriate temperature can be selected by taking into consideration the quantity of heat needed to be removed for maintaining the reaction temperature at a constant level within the range of from 100° C. to 200° C., the difference between the reaction temperature and the temperature of the heat exchange medium ($\Delta T$), the heat transfer area and the flow rates of the process liquid and the heat exchange medium. In the process of the present invention, it is preferred that an occurrence of foulings on the inner wall of the process-side channel of the heat exchanger is prevented during the reaction by flowing the reaction mixture obtained by the reaction of an alkylene oxide with carbon dioxide as the process liquid through the circulation circuit including the reactor and the process-side channel of the heat exchanger while flowing the heat exchange medium having a temperature of from 140° C. to 200° C., preferably from 140° C. to 180° C., through the heat exchange-side channel of the heat exchanger, thereby maintaining the inner temperature of the process-side channel at a level within the range of from 135° C. to 200° C., preferably from 135° C. to 180° C.

In the process of the present invention, almost no foulings occur on the inner wall of the process-side channel of the heat exchanger when the heat exchange medium flowed through the heat exchange-side channel of the heat exchanger has a temperature of from 140° C. to 200° C. and the inner temperature of the process-side channel is maintained at a level within the range of from 135° C. to 200° C. However, when a heat exchange medium has a temperature lower than 140° C., the foulings occur in the heat exchanger and it becomes necessary to increase the amount of the heat exchange medium fed to the heat exchanger so as to maintain the heat removing ability of the heat exchanger. However, due to various problems, such as a limited power of the feeding pump and a pressure loss of the piping, there is a limit with respect to an increase in the amount of the heat exchange medium which can be fed to the heat exchanger. Therefore, the heat removing ability of the heat exchanger would inevitably be lowered to a level such that the reaction temperature cannot be maintained at a predetermined level and, finally, it becomes impossible to continue the operation of the production system. On the other hand, when a heat exchange medium having a temperature higher than 200° C. is used to remove the heat of reaction from the reaction mixture, it becomes difficult to maintain the reaction temperature at 200° C. or lower. Further, adverse side reactions are likely to occur and the safety of the reaction system becomes lowered due to the increase in the alkylene oxide concentration in the gaseous phase in the reactor.

In the present invention, when foulings occur on the inner wall of the process-side channel of the heat exchanger during the reaction of an alkylene oxide with carbon dioxide for producing an alkylene carbonate, so that the heat removing ability of the heat exchanger becomes lowered, it is preferred that, after the reaction, a washing liquid is flowed as the process liquid to thereby wash-away fouls having adhered to the inner wall of the process-side channel of the heat exchanger. Specifically, after the reaction for producing an alkylene carbonate, fouls having adhered to the heat exchanger can be washed-away by a method comprising (1) withdrawing the reaction mixture from the reactor to thereby empty the reactor; (2) charging a washing liquid into the reactor; and (3) flowing the washing liquid through the circulation circuit including the reactor and the process-side channel of the heat exchanger while flowing the heat exchange medium having a temperature of from 140° C. to 200° C., preferably from 140° C. to 180° C., through the heat exchange-side channel of the heat exchanger, thereby maintaining the inner temperature of the process-side channel at a level within the range of from 135° C. to 200° C., preferably from 135° C. to 180° C. By this method, it becomes possible to easily wash-away the fouls having adhered to the inner wall of the process-side channel of the heat exchanger within a short period of time without the need to disassemble the heat exchanger. Therefore, the production of an alkylene carbonate can be restarted within a short period of time after the production is temporarily stopped for the above-mentioned washing operation for recovering the heat removing ability of the heat exchanger. The process of the present invention, in which a washing liquid is flowed as the process liquid to thereby wash-away fouls having adhered to the inner wall of the process-side channel of the heat exchanger, can be performed before the reaction for producing an alkylene carbonate, if necessary.

The washing liquid used for washing the heat exchanger is used not for dissolving therein the fouls containing the viscous polymeric substances, but for decomposing the fouls at specific temperatures and diffusing therein the decomposed fouls. Therefore, there is no particular limitation with respect to the substance used as the washing liquid in the present invention so long as the substance is in a liquid state at the inner temperature (namely, 135° C. to 200° C.) of the process-side channel of the heat exchanger during the washing. Preferred washing liquids are water (which is easily available and advantageous from the viewpoint of waste disposal) and ethylene carbonate (which can be easily recovered by distillation as a desired product of the process of the present invention). It is especially preferred to use ethylene carbonate as a washing liquid after the production of ethylene carbonate. In this instance, when ethylene carbonate is used as a washing liquid, the residual washing liquid would not cause any problem and, thus, there is no need to dry the inside of the reactor after washing.

For easily stripping off the residual fouls (mostly polymeric substances which are no longer viscous) from the process-side channel of the heat exchanger, it is preferred that the temperature of the washing liquid flowing through the process-side channel of the heat exchanger is elevated and then lowered or vice versa so as to cause the heat transfer tube (as the process-side channel of the heat exchanger) to expand and then contract or vice versa. In this technique, the larger the difference between the lowest and highest temperatures of the washing liquid, the larger the expansion and contraction of the heat transfer tube. Therefore, this technique becomes more effective when the difference between the lowest temperature and the highest temperature is large. However, a very large temperature difference is not preferred because changing of the temperature of the washing liquid becomes time consuming. For example, the temperature of the washing liquid can be changed in the above-mentioned manner, wherein 100° C. and 150° C. are used as the lowest temperature and the highest temperature, respectively.

In the present invention, either the heat exchanger alone or the whole circulation circuit (in which the reactor is communicating with the process-side channel of the heat exchanger through a piping) may be washed in the above-mentioned manner. It is considered that fouling comprising viscous polymeric substances (which are similar to those found in the heat exchanger) are likely to occur at portions of the circulation circuit which have a low temperature due to heat dissipation and the like. Therefore, it is preferred that the washing liquid is flowed through the whole circulation circuit so as to decompose and strip off the fouls having adhered to the inner wall thereof. The portions of the circulation circuit which have a low temperature due to heat dissipation and the like include nozzles of measuring instruments (e.g., a thermometer, a level gage, a pressure gage, and a flow meter), a nozzle for sampling, a flange of a joint of pipings, a hood of a valve, a gas exhaust nozzle and a liquid withdrawal nozzle of a circulation pump, and a strainer.

The above-mentioned washing of a heat exchanger can be performed not only after the production of an alkylene carbonate by the process of the present invention in which, during the reaction, the reaction mixture obtained by the reaction of an alkylene oxide with carbon dioxide is flowed as the process liquid to thereby prevent foulings from occurring on the inner wall of the process-side channel of the heat exchanger, but also after the production of an alkylene carbonate by any processes for producing an alkylene carbonate which use a heat exchanger for controlling the reaction temperature.

BEST MODE FOR CARRYING OUT THE INVENTION

Hereinbelow, the present invention will be described in more detail with reference to the following Examples and Comparative Example, but they should not be construed as limiting the scope of the present invention.

EXAMPLE 1

Figure 1:
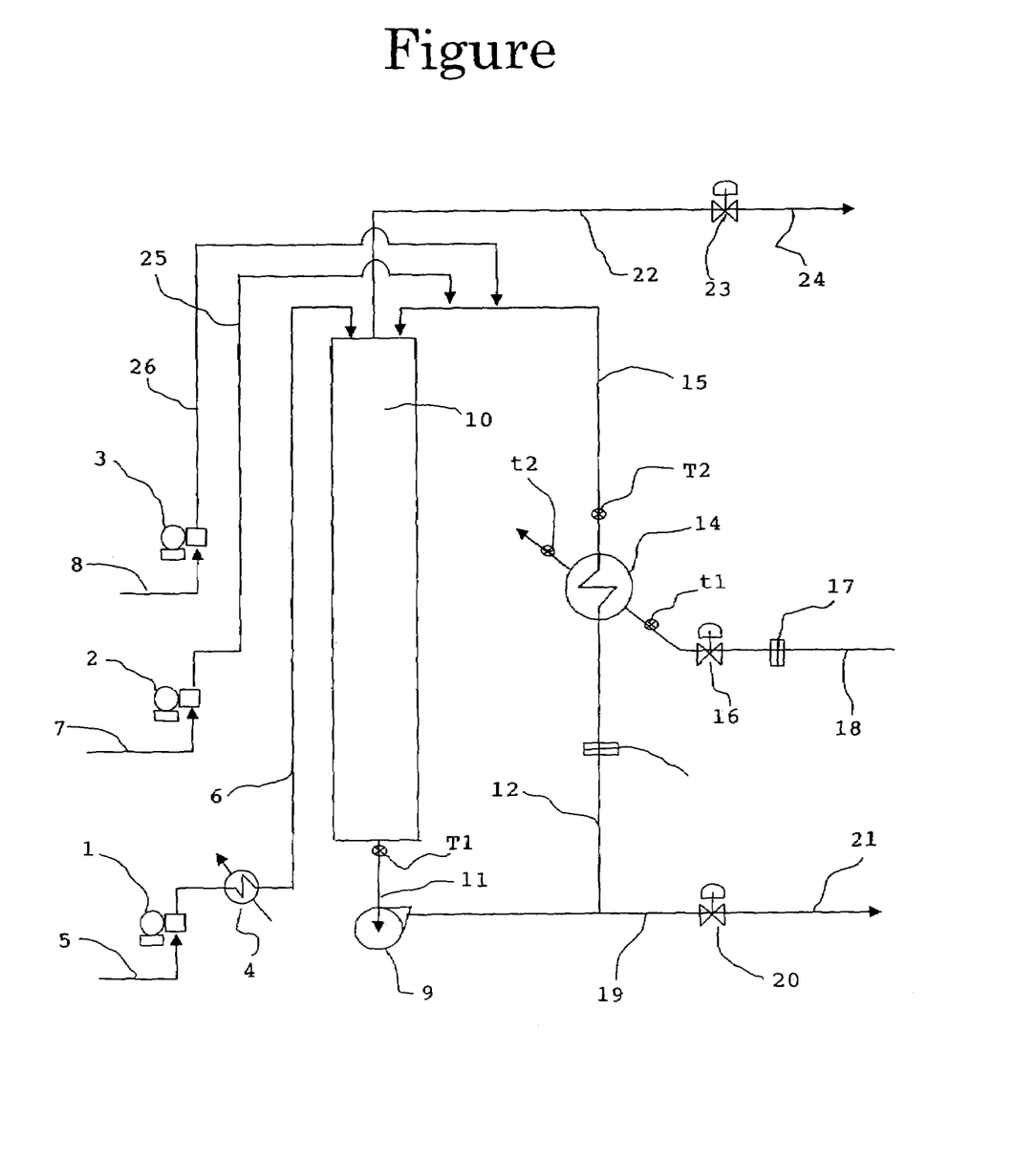
FIG. 1 is a schematic diagram of a production system used in Example 1 below for performing a process for continuously producing an alkylene carbonate.

Ethylene carbonate was produced using the production system shown in FIG. 1.

Reactor 10 was a vertical reaction column made of stainless steel (inner diameter: 1.6 m φ, length of the cylindrical portion: 8 m, volume: 20 m$^3$), wherein a liquid spraying nozzle for increasing the efficiency of absorption of carbon dioxide by a liquid was provided at the upper portion of the reactor. In the production system, reactor 10 communicated with a process-side channel of heat exchanger 14 through a piping to form a circulation circuit. Heat exchanger 14 was a single-pass heat exchanger comprising a shell having accommodated therein 172 tubes (heat transfer area: 147.6 m$^2$, outer diameter of each tube: 42.7 mm φ, and tube length: 6.95 m), wherein a process liquid was flowed through the tubes (process-side channels) and a heat exchange medium was flowed through the shell space (i.e., space between the tubes and the inner wall of the shell) as a heat exchange-side channel. A heat transfer oil (trade name: KSK-oil-280, manufactured and sold by Soken Chemical & Engineering Co., Ltd., Japan) was fed as a heat exchange medium to the heat exchange-side channel (shell space) of heat exchanger 14. The heat transfer oil was used not only as a heating medium at the start of the reaction but also as a coolant during the stationary operation of the production system.

As one of the raw materials, ethylene oxide (cooled to 5° C.) was fed through pipe 7 to ethylene oxide pump 2 in which the ethylene oxide was pressurized. From ethylene oxide pump 2, the pressurized ethylene oxide was fed through pipes 25 and 15 to reactor 10 at a flow rate of 2,500 kg/hr. With respect to carbon dioxide which is another raw material, a liquefied carbon dioxide was fed through pipe 5 to carbon dioxide feeding pump 1. The liquefied carbon dioxide was pressurized in pump 1 and fed to a water bath-type carbon dioxide evaporator 4 to vaporize the liquefied carbon dioxide. The vaporized carbon dioxide (carbon dioxide gas) having a temperature of about 90° C. was fed through pipe 6 to the gaseous phase in the upper portion of reactor 10 so as to maintain the pressure in reactor 10 at a constant level of about 9.5 MPa. An average carbon dioxide feeding rate was 2,700 kg/hr.

During the operation, the pressure in reactor 10 sometimes reached or exceeded 10 MPa. In such cases, gas control valve 23 connected to the vent of reactor 10 was opened so as to discharge gas from the gaseous phase of reactor 10 through pipes 22 and 24, thereby decreasing the pressure in reactor 10.

As a catalyst, potassium iodide (KI) in the form of a 5% by weight solution thereof in ethylene carbonate was used. More specifically, 9 parts by weight of a recycled catalyst (recovered after purifying an ethylene carbonate product) and 1 part by weight of a fresh catalyst solution were mixed, and the resultant catalyst solution was fed through pipe 8 to catalyst feeding pump 3. From catalyst feeding pump 3, the catalyst solution was fed through pipes 26 and 15 to reactor 10. The feeding rate of the catalyst solution was adjusted to 274 kg/hr by means of catalyst feeding pump 3 so that the potassium iodide concentration of the reaction system became 0.23 to 0.26% by weight.

The resultant reaction mixture was withdrawn from reactor 10 so as to maintain the volume of the reaction mixture in the reactor at a constant level of 14.5 tons. The amount of the withdrawn reaction mixture was controlled by means of control valve 20 for withdrawing a reaction mixture, and the reaction mixture was withdrawn through pipes 19 and 21.

The production of ethylene carbonate was performed under conditions wherein the reaction temperature measured using thermometer T1 provided at the bottom portion of reactor 10 was in the range of from 176° C. to 177° C. During the reaction, the process liquid was flowed through the circulation circuit including reactor 10 and the process-side channel of heat exchanger 14, while flowing a heat exchange medium through the heat exchange-side channel of heat exchanger 14. Specifically, the reaction mixture was withdrawn from the outlet of reactor 10 and pressurized using circulation pump 9 of the reactor. The pressurized reaction mixture was fed through pipes 11 and 12 to heat exchanger 14. The reaction mixture having its temperature controlled using heat exchanger 14 was returned through pipe 15 to reactor 10 at the inlet thereof, to thereby circulate the reaction mixture through the circulation circuit. The amount of the circulated reaction mixture was monitored using circulation flow meter 13 of the reactor and maintained at a constant rate of about 400 tons/hr. As a result, the average retention time in reactor 10 became 2.65 hr and the number of circulation became 28 times/hr.

In heat exchanger 14, the flow rate of the heat exchange medium flowing through heat exchanger 14 was controlled automatically by means of temperature control valve 16 to thereby maintain the temperature of the reaction mixture at a constant level of 173° C., wherein the reaction temperature was measured by thermometer T2 provided at the outlet of heat exchanger 14. The heat exchange medium was fed through pipe 18 to the shell space of heat exchanger 14. The temperature of the heat exchange medium fed to heat exchanger 14 was initially maintained at 140° C., and 23 days after the start of the operation, the temperature was elevated to 145° C. The temperature of the heat exchange medium was measured by thermometer t1 provided at an inlet of heat exchanger 14 for the heat exchange medium, and the change in flow rate of the heat exchange medium was monitored using flow meter 17. (The temperature measured by thermometer t2 provided at the outlet of heat exchanger 14 for the heat exchange medium was also recorded for calculating the overall heat transfer coefficient (U).)

Thus, the temperature of the reaction mixture (i.e., the temperature measured with thermometer T2) was controlled automatically using the outlet temperature of heat exchanger 14. As a result, the temperature measured with thermometer T1 provided at the bottom portion of reactor 10 became almost constant at a level within the range of from about 176° C. to 177° C.

The ethylene oxide concentration in the gaseous phase of reactor 10 was measured using an online gas chromatograph as a continuous analyzer to monitor the conversion of ethylene oxide and to detect any disorder in the production system at an early stage. The ethylene oxide concentration determined using the continuous analyzer was within the range of from 3 to 5% by volume, based on the volume of the gaseous phase in the reactor.

The amount of the ethylene carbonate produced was 4,970 to 4,990 kg/hr (4,978 kg/hr in average).

The occurrence of foulings and the heat removing ability of heat exchanger 14 were evaluated using the overall heat transfer coefficient (U) which is calculated by the following formula:

$$U = Q/\{A \times (\Delta T)_{lm}\}$$

wherein:

U: overall heat transfer coefficient (kJ/m²·hr·° C.)

Q: rate of heat transfer (kJ/hr)=(flow rate in the process-side channel)×($T_1-T_2$)×specific heat A: heat transfer area=147.6 m²

$(\Delta T)_{lm}$: logarithmic mean temperature difference=$\{(T_1-t_1)-(T_2-t_2)\}/\ln\{(T_1-t_1)/(T_2-t_2)\}$ wherein $T_1$, $T_2$, $t_1$ and $t_2$ are the temperatures measured by thermometers T1, T2, t1 and t2, respectively.

The overall heat transfer coefficient (U) of heat exchanger 14 was calculated using the specific heat (i.e., 2.00 kJ/kg·° C.) of the process liquid, which is the reaction mixture containing ethylene carbonate.

The overall heat transfer coefficients (U) of heat exchanger 14 during the production of ethylene carbonate are shown in Table 1.

TABLE 1

| Date of operation | Temperature of heat exchange medium (° C.) | Overall heat transfer coefficient (KJ/m²·Hr·° C.) |
| --- | --- | --- |
| 1st day | 140° C. | 703 |
| 14th day | 140° C. | 707 |
| 22nd day | 140° C. | 703 |
| 23rd day | changed to 145° C. | — |
| 25th day | 145° C. | 782 |
| 38th day | 145° C. | 799 |
| 54th day | 145° C. | 812 |
| 68th day | 145° C. | 808 |

As apparent from Table 1 above, lowering of the overall heat transfer coefficient (U) was not observed when the temperature of the heat exchange medium fed to the heat exchanger was maintained at 140° C. When the temperature of the heat exchange medium was elevated to 145° C., the overall heat transfer coefficient (U) increased slightly in accordance with the progress of the operation and, therefore, it is considered that fouls having occurred and adhered to the heat exchanger were washed-away by elevating the temperature of the heat exchange medium. Thus, by the process of the present invention, it becomes possible to produce ethylene carbonate continuously and stably for a long period of time.

Comparative Example 1

Ethylene carbonate was produced in substantially the same manner as in Example 1 except that the temperature of the heat exchange medium fed to heat exchanger 14 was maintained at a level within the range of from 100° C. to 130° C.

The amount of the ethylene carbonate produced was 4,970 to 4,990 kg/hr (4,978 kg/hr in average).

The overall heat transfer coefficients (U) of heat exchanger 14 during the production of the ethylene carbonate are shown in Table 2 below.

TABLE 2

| Date of operation | Temperature of heat exchange medium (° C.) | Overall heat transfer coefficient (KJ/m²·Hr·° C.) |
| --- | --- | --- |
| 3rd day | 130° C. | 703 |
| 10th day | 130° C. | 586 |
| 20th day | 130° C. | 519 |
| 21st day | changed to 125° C. | — |
| 24th day | 125° C. | 477 |
| 25th day | changed to 120° C. | — |
| 39th day | 120° C. | 418 |
| 43rd day | changed to 112° C. | — |
| 48th day | 112° C. | 339 |

As apparent from Table 2 above, when the temperature of the heat exchange medium was lower than 140° C., the overall heat transfer coefficient (U) decreased gradually during the production of the ethylene carbonate. As a consequence, the removal of the heat of reaction became insufficient, so that the desired reaction temperature (173° C.) could not be maintained and a rise in temperature (to about 174° C. to 175° C.) was observed. Therefore, the reaction was terminated on the 50th day. Although the amount of the produced ethylene carbonate was the same as in Example 1, ethylene carbonate could not be produced stably for a long period of time.

EXAMPLE 2

Ethylene carbonate was produced in substantially the same manner as in Example 1, except that the temperature of the heat exchange medium fed to heat exchanger 14 was maintained at a level within the range of from 100° C. to 120° C. As a result, the overall heat transfer coefficient (U) which was 705 kJ/m² hr·° C. on the 2nd day was decreased to 372 kJ/m² hr·° C. on the 38th day. Since a further increase in the feeding rate of the heat exchange medium was difficult, the reaction was stopped and heat exchanger 14 was washed in the following manner.

Water was used as a washing liquid. First, all of the reaction mixture contained in reactor 10 was withdrawn therefrom and, then, reactor 10 was filled with 13 tons of a hot water having a temperature of 70° C. The hot water was pressurized using circulation pump 9 of the reactor and circulated through the circulation circuit while adjusting the flow rate to approximately 400 tons/hr as measured by circulation flow meter 13. After the start of the circulation of the washing liquid, the gaseous phase in reactor 10 was pressurized to about 0.8 MPa using nitrogen gas, and gas control valve 23 provided at a vent of reactor 10 was closed completely. Subsequently, the heat exchange medium having a temperature of 160° C. to 180° C. was fed to the shell space of heat exchanger 14 so as to elevate the temperature of the washing liquid at a rate of about 30° C./hr. When the temperature of the washing liquid circulating in the circulation circuit reached 160° C., this temperature was maintained for approximately 1.5 hours. Subsequently, the washing liquid was cooled at a rate of about 50° C./hr, and when the temperature of the washing liquid was lowered to about 100° C., this temperature was maintained for 0.5 hour. A cycle of heating the washing liquid to about 160° C., maintaining this temperature for 1.5 hours, cooling the washing liquid to about 100° C. and maintaining this temperature for 0.5 hour in the above-mentioned manners was repeated five times, thereby washing heat exchanger 14.

Approximately 0.7 kg of black, free-flowing microparticles were accumulated inside the strainer of circulation pump 9 after washing of heat exchanger 14.

After withdrawing all of the washing liquid contained in reactor 10 from the circulation circuit, production of ethylene carbonate was resumed and performed in the same manner as mentioned above. The amount of the produced ethylene carbonate was 4,978 kg/hr. The overall heat transfer coefficient (U) was determined on the 2nd day when the operation of the reaction system became stationary. The overall heat transfer coefficient (U), which was 372 kJ/m²·hr·° C. before washing, was recovered to 711 kJ/m²·hr·° C. This means that fouls having adhered to the inner wall of the process-side channel of the heat exchanger were satisfactorily removed by the washing performed for only a short period of time.

EXAMPLE 3

Ethylene carbonate was produced in substantially the same manner as in Example 1, except that the temperature of the heat exchange medium fed to heat exchanger 14 was maintained at a level within the range of from 100° C. to 130° C. As a result, it was found that the overall heat transfer coefficient (U), which was 708 kJ/m²·hr·° C. on the 2nd day, was decreased to 398 kJ/m²·hr·° C. on the 40th day. Since a further increase in the feeding rate of the heat exchange medium was difficult, the reaction was stopped and heat exchanger 14 was washed in the following manner.

Ethylene carbonate was used as a washing liquid and the washing was performed in substantially the same manner as in Example 2. Specifically, the reaction mixture contained in reactor 10 was withdrawn from the circulation circuit and reactor 10 was filled with 14.5 tons of ethylene carbonate. The ethylene carbonate was pressurized using circulation pump 9 of the reactor and circulated through the circulation circuit while adjusting the flow rate to approximately 400 tons/hr by means of circulation flow meter 13. After start of the circulation of the washing liquid, the gaseous phase in reactor 10 was pressurized to about 0.8 MPa using nitrogen gas, and gas control valve 23 provided at a vent of reactor 10 was closed completely. Subsequently, the heat exchange medium having a temperature of 160° C. to 180° C. was fed to the shell space of heat exchanger 14 so as to elevate the temperature of the washing liquid at a rate of about 30° C./hr. When the temperature of the washing liquid circulating in the circulation circuit reached 155° C., this temperature was maintained for approximately 1.5 hours. Subsequently, the washing liquid was cooled at a rate of about 50° C./hr, and when the temperature of the washing liquid was lowered to about 100° C., this temperature was maintained for 15 minutes. This cycle of heating and cooling the washing liquid was repeated five times, thereby washing heat exchanger 14.

Approximately 0.3 kg of black, free-flowing microparticles were accumulated inside the strainer of circulation pump 9 after the washing of heat exchanger 14.

After withdrawing all of the washing liquid contained in reactor 10 from the circulation circuit, production of ethylene carbonate was resumed and performed in the same manner as mentioned above. The amount of the produced ethylene carbonate was 4,978 kg/hr. The overall heat transfer coefficient (U) was determined on the 2nd day when the operation of the reaction system became stationary. The overall heat transfer coefficient (U), which was 398 kJ/m²·hr·° C. before washing, was recovered to 703 kJ/m²·hr·° C. This means that the fouls having adhered to the inner wall of the process-side channel of the heat exchanger were satisfactorily removed by the washing performed for only a short period of time.

Further, the ethylene carbonate used as the washing liquid was purified, to thereby obtain an ethylene carbonate product having a desired purity. In this Example, since ethylene carbonate, which is the desired product, was used as the washing liquid, no adverse effects were caused by the washing liquid remaining inside the reactor and, hence, there was no need to dry the reactor after washing.

INDUSTRIAL APPLICABILITY

When an alkylene carbonate is produced by the process of the present invention, it becomes possible to prevent foulings from occurring on the inner wall of the process-side channel of the heat exchanger. Therefore, the heat removing ability of the heat exchanger is not lowered, thereby enabling the stable, continuous production of an alkylene carbonate for a long period of time. In addition, even when foulings occur on the inner wall of the process-side channel of the heat exchanger, fouls having occurred and adhered to the inner wall of the process-side channel of the heat exchanger can be easily washed-away within a short period of time without disassembling the heat exchanger. Therefore, it becomes possible to recover the heat removing ability of the heat exchanger and resume the production of the alkylene carbonate, easily.

The invention claimed is:

1. A process for producing an alkylene carbonate, which comprises reacting an alkylene oxide represented by the following formula (1):

(1)

wherein each of $R^1$, $R^2$, $R^3$ and $R^4$ independently represents a hydrogen atom, a $C_1$–$C_8$ straight chain hydrocarbon group, a $C_3$–$C_8$ alicyclic hydrocarbon group or a $C_6$–$C_8$ aromatic hydrocarbon group,
with carbon dioxide in the presence of a catalyst in a reactor to obtain a reaction mixture in said reactor, wherein said reaction mixture contains an alkylene carbonate represented by the following formula (2):

(2)

wherein $R^1$, $R^2$, $R^3$ and $R^4$ are as defined for formula (1), said reactor communicating with a process-side channel of a heat exchanger through a piping to form a circulation circuit, wherein said heat exchanger has a heat exchange-side channel for flowing therethrough a heat exchange medium having a temperature controlled in a predetermined range and has said process-side channel for flowing therethrough a process liquid which is heat exchanged with said heat exchange medium in association with the process for producing an alkylene carbonate, characterized in that the process further comprises, during or after the reaction, flowing said process liquid through said circulation circuit including the reactor and the process-side channel of the heat exchanger while flowing said heat exchange medium having a temperature of from 140° C. to 200° C. through said heat exchange-side channel of the heat exchanger, thereby maintaining the inner temperature of said process-side channel at a level within the range of from 135° C. to 200° C.

2. The process according to claim 1, wherein, during the reaction, the reaction mixture obtained by the reaction of an alkylene oxide with carbon dioxide is flowed as said process liquid.

3. The process according to claim 1, wherein, after the reaction, a washing liquid is flowed as said process liquid.

4. The process according to claim 1, wherein said alkylene oxide is ethylene oxide and said alkylene carbonate is ethylene carbonate.

5. The process according to claim 2, wherein said alkylene oxide is ethylene oxide and said alkylene carbonate is ethylene carbonate.

6. The process according to claim 3, wherein said alkylene oxide is ethylene oxide and said alkylene carbonate is ethylene carbonate.

* * * * *